(12) United States Patent
Auweter et al.

(10) Patent No.: US 6,296,877 B1
(45) Date of Patent: Oct. 2, 2001

(54) STABLE, AQUEOUS DISPERSIONS AND STABLE, WATER-DISPERSIBLE DRY XANTHOPHYLL POWDER, THEIR PRODUCTION AND USE

(75) Inventors: Helmut Auweter, Limburgerhof; Heribert Bohn, Wattenheim; Erik Lüddecke, Mutterstadt, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/319,600

(22) PCT Filed: Dec. 1, 1997

(86) PCT No.: PCT/EP97/06712

§ 371 Date: Jun. 8, 1999

§ 102(e) Date: Jun. 8, 1999

(87) PCT Pub. No.: WO98/26008

PCT Pub. Date: Jun. 18, 1998

(30) Foreign Application Priority Data

Dec. 12, 1996 (DE) .............................. 196 51 681

(51) Int. Cl.$^7$ ...................................... A61K 9/16
(52) U.S. Cl. .................. 424/490; 424/489; 424/491; 424/492; 424/493; 424/496
(58) Field of Search .................... 424/489, 490, 424/491, 492, 493, 496

(56) References Cited

U.S. PATENT DOCUMENTS

| 3,110,598 | 11/1963 | Mueller . |
| 3,227,561 | 1/1966 | Mima et al. . |
| 3,886,294 | 5/1975 | Emodi et al. . |
| 4,522,743 | 6/1985 | Horn et al. . |
| 4,726,955 | 2/1988 | Horn et al. . |
| 5,364,563 | 11/1994 | Cathrein et al. . |

FOREIGN PATENT DOCUMENTS

| 599 196 | 1/1988 | (AU) . |
| 1 211 911 | 8/1960 | (DE) . |
| 1 288 713 | 2/1969 | (DE) . |
| 2 411 529 | 9/1974 | (DE) . |
| 65 193 | 11/1982 | (EP) . |
| 239 949 | 10/1987 | (EP) . |
| 278 284 | 8/1988 | (EP) . |
| 410 236 | 1/1991 | (EP) . |
| 91/06292 | 5/1991 | (WO) . |
| 94/19411 | 9/1994 | (WO) . |

OTHER PUBLICATIONS

Registry No. 9000–70–8, American Chemical Society 2001. [online][retrieved on May 10, 2001]. Retrieved from STN Database, File Registry.*
Rompps Chemielexikon, 1981, 919, 1427.

* cited by examiner

Primary Examiner—Thurman K. Page
Assistant Examiner—P. E. McQueeney
(74) Attorney, Agent, or Firm—Keil & Weinkauf

(57) ABSTRACT

Preparation of a stable aqueous dispersion, or a stable water-dispersible dry powder, of xanthophylls, which comprises a) preparing a molecularly dispersed solution of at least one xanthophyll, with or without an emulsifier and/or an edible oil, in a water-miscible organic solvent, or a mixture of water and a water-miscible organic solvent, at above 30° C., b) mixing this solution with an aqueous solution of a mixture of protective colloids,
  b$_1$) in which the mixture comprises at least one low-molecular-weight protective colloid component and at least one high-molecular-weight protective colloid component, whose mean molecular weights differ by at least 10,000,
  b$_2$) the solvent component being transferred to the aqueous phase and the hydrophobic phase of the xanthophyll being formed as a nanodispersed phase c) and if appropriate, to prepare a water-dispersible dry powder, freeing the resulting dispersion from the solvent and the water and drying it in the presence or absence of a coating material.

8 Claims, No Drawings

STABLE, AQUEOUS DISPERSIONS AND STABLE, WATER-DISPERSIBLE DRY XANTHOPHYLL POWDER, THEIR PRODUCTION AND USE

The carotenoid class of compounds is classified into two main groups: carotenes and xanthophylls. In contrast to carotenes, which are pure polyene hydrocarbons, such as β-carotene or lycopene, xanthophylls additionally contain oxygen functions such as hydroxyls, epoxy and/or oxo groups. Typical representatives of this group are, inter alia, astaxanthin, canthaxanthin and zeaxanthin.

Xanthophylls are very common in nature and occur, inter alia, in corn (zeaxanthin), in green beans (lutein), in paprika (capsanthin), in egg yolk (lutein) and also in crustaceans and salmon (astaxanthin), and they give their characteristic color to these foods.

These polyenes, some of which can be synthesized industrially and which can be isolated from natural sources, are important colorants for the food and feed industries and for the pharmaceutical sector as a substitute for synthetic dyes.

All xanthophylls are insoluble in water, whereas in fats and oils a still only low solubility is found. This limited solubility and the high sensitivity to oxidation impede direct use of the relatively coarse-grained products obtained from synthesis in coloring foods and feeds, since the substances in coarsely crystalline form give only poor coloring results. These effects which are disadvantageous for the practical use of xanthophylls are displayed, in particular, in an aqueous medium, since the xanthophylls are completely insoluble therein.

Improved color yields in the direct coloring of foods can only be achieved by specifically prepared formulations in which the active compounds are present in finely divided form with or without protection from oxidation by protective colloids. In addition, these formulations used in feeds lead to a higher bioavailability of the xanthophylls and thus indirectly to improved coloring effects, eg. in pigmenting egg yolk or fish.

To improve the color yields and to increase the absorbability or bioavailability, various processes have been described, all of which have the purpose of decreasing the crystallite size of the active compounds and bringing it to a particle size range of less than 10 μm.

Numerous methods, inter alia described in Chimia 21 (1967) 329, WO 91/06292 and in WO 94/19411, make use of grinding carotenoids using a colloid mill and thereby achieve particle sizes of from 2 to 10 μm.

In addition, there are a number of combined emulsifying/spray-drying processes, as described, for example, in DE-A-12 11 911 or in EP-A-0 410 236.

According to EP-B-0 065 193, finely divided pulverulent β-carotene preparations are prepared by dissolving β-carotene in a volatile water-miscible organic solvent at from 50° C. to 200° C., if appropriate under elevated pressure, in the course of a period of less than 10 seconds. The β-carotene is precipitated out of the resulting molecularly dispersed solution at from 0° C. to 50° C., by immediate rapid mixing with an aqueous solution of a protective colloid. In this manner, a colloidally dispersed β-carotene hydrosol of orange-yellow hue is obtained. Subsequent spray-drying of the dispersion gives a free-flowing dry powder which dissolves in water, with formation of a clear yellow-orange dispersion.

However, the following phenomena may be observed with the nanoparticular active compound dispersions of xanthophylls prepared according to EP-B-0 065 193.

The aqueous xanthophyll-containing active compound dispersions are frequently colloidally unstable, in particular when they are being concentrated. Owing to flocculation of the active compound particles, some of which sediment, some of which cream, further conversion of the dispersion into a dry powder is no longer possible.

In the case of xanthophylls having carbonyl functions, in addition, the gelatin used as sole protective colloid can crosslink, so that a gel is formed which can no longer be redispersed and which likewise can not be further converted into a dry powder.

The high demands placed on xanthophyll-containing formulations with respect to coloring action and bioavailability can thus not always be complied with because of the problems described with the abovementioned process.

It is an object of the present invention to propose a process for preparing a stable aqueous dispersion of xanthophylls. In addition, stable pulverulent xanthophyll preparations should be provided by which a good coloring action and, in addition, a high bioavailability can be achieved.

We have found that this object is achieved according to the invention by a process for preparing a stable aqueous dispersion, or a stable water-dispersible dry powder, of xanthophylls, which comprises a) preparing a molecularly dispersed solution of at least one xanthophyll, with or without an emulsifier and/or an edible oil, in a water-miscible organic solvent, or a mixture of water and a water-miscible organic solvent, at above 30° C., b) mixing this solution with an aqueous solution of a mixture of protective colloids, $b_1$) in which the mixture comprises at least one low-molecular-weight protective colloid component and at least one high-molecular-weight protective colloid component whose mean molecular weights differ by at least 10,000, $b_2$) the solvent component being transferred to the aqueous phase and the hydrophobic phase of the xanthophyll being formed as a nanodisperse phase c) and if appropriate, to prepare a water-dispersible dry powder, freeing the resulting dispersion from the solvent and the water and drying it in the presence or absence of a coating material.

The present invention also relates to stable xanthophyll-containing cold-water-dispersible dry powders which may be used exceptionally well for coloring foods and feeds and administered forms of pharmaceuticals.

The preparations according to the invention are generally prepared in such a manner that the xanthophyll(s), with or without an emulsifier and/or an edible oil, is/are dissolved in a water-miscible organic solvent at preferably from 50° C. to 240° C., in particular from 100° C. to 200° C., particularly preferably from 140° C. to 180° C., if appropriate under pressure.

Since the action of high temperatures can decrease the desired high all-trans proportion of isomer, the xanthophyll(s) is/are dissolved very quickly, for example in a matter of seconds, eg. in from 0.1 to 10 seconds, particularly preferably in less than 1 second. To prepare the molecularly dispersed solution quickly, employing elevated pressure, eg. in the range from 20 bar to 80 bar, preferably from 30 to 60 bar, can be advantageous.

The resulting molecularly dispersed solution is admixed immediately afterward with the cooled or uncooled aqueous solution of a protective colloid, preferably in such a manner that a mixing temperature of from about 35° C. to 80° C. is established.

In the course of this, the solvent component is transferred to the aqueous phase and the hydrophobic phase of the xanthophyll(s) is formed as a nanodisperse phase.

As regards a more detailed description of process and apparatus, EP-B-0 065 193 is herein expressly incorporated by reference.

Surprisingly, it has now been found that colloidally stable and non-crosslinking nanoparticular active compound dispersions of xanthophylls are obtained if, other than in the formulation processes described hitherto, in the abovementioned precipitation of one or more molecularly dispersed dissolved xanthophylls first of all an aqueous protective colloid dispersion of at least one low-molecular-weight component is used and then a further aqueous protective colloid dispersion of at least one high-molecular-weight component is added, the mean molecular weights of the low- and high-molecular-weight polymers differing by at least 10,000, preferably by at least 30,000.

However, it is also possible to carry out the two-stage precipitation in one step in a mixture of at least one low-molecular-weight component and at least one high-molecular-weight component, whose mean molecular weights differ by at least 10,000, preferably by at least 30,000.

The protective colloids used are low- and high-molecular-weight components of, for example, gelatin, fish gelatin, starch, dextrin, plant proteins, pectin, gum arabic, casein, caseinate or mixtures of these, the protein-containing protective colloids, in particular non-gelling low-molecular-weight protein hydrolysates and higher-molecular-weight gelling gelatins being preferred. However, poly(vinylalcohol), polyvinylpyrrolidone, methyl cellulose, carboxymethyl cellulose, hydroxypropyl cellulose and alginates can also be used. The mean molecular weight ($M_w$) of the low-molecular-weight protective colloid component is preferably from 10,000 to 50,000, in particular from 15,000 to 30,000, whereas the high-molecular-weight component has a mean molecular weight of preferably greater than 60,000. The proportion of the low-molecular-weight protective colloid component is from 5 to 95% by weight, preferably from 20 to 80% by weight, in particular from 30 to 60% by weight. To increase the mechanical stability of the end product, it is expedient to admix the colloid with a softener, such as sugars or sugar alcohols, eg. sucrose, glucose, lactose, invert sugar, sorbitol, mannitol or glycerol. The ratio of protective colloid and softener to xanthophyll solution is generally selected in such a manner that the end product obtained comprises from 0.5 to 20% by weight, preferably 10% by weight, of xanthophyll, from 10 to 50% by weight of a protective colloid, from 20 to 70% by weight of a softener, all percentages being based on the dry mass of the powder, and with or without small amounts of a stabilizer.

The xanthophylls which can be used for carrying out the invention are the known obtainable natural or synthetic representatives of this class of compounds which are usable as coloring means, eg. astaxanthin, zeaxanthin, canthaxanthin, capsanthin and lutein.

To increase the stability of the active compound to oxidative decay, it is advantageous to add stabilizers such as α-tocopherol, t-butylated hydroxytoluene, t-butylated hydroxyanisole, ascorbic acid or ethoxyquin. They can be added either to the aqueous phase or to the solvent phase, but preferably they are dissolved together with the colorants, with or without additional emulsifiers, in the solvent phase. Emulsifiers which can be used are, for example, ascorbyl palmitate, polyglycerol fatty acid esters, sorbitan fatty acid esters, propylene glycol fatty acid esters or lecithin in a concentration of from 0 to 200% by weight, preferably from 10 to 150% by weight, particularly preferably from 20 to 80% by weight, based on the xanthophyll(s).

In some circumstances, it may also be advantageous to dissolve additionally in the solvent phase a physiologically approved oil such as sesame oil, corn oil, cotton seed oil, soybean oil or peanut oil and esters of medium-chain vegetable fatty acids in a concentration of from 0 to 500% by weight, preferably from 10 to 300% by weight, particularly preferably from 20 to 100% by weight, based on the xanthophyll(s), which oil is then precipitated out in extremely finely divided form, together with the active compounds and said additives, on mixing with the aqueous phase.

Depending on the type and amount of the protective colloid used, a deep-colored viscous liquid is obtained. The solvent can be removed, for example, by extracting with a water-immiscible solvent or, depending on boiling point, in a manner known per se, eg. by distillation, if appropriate under reduced pressure. In this case, it has proved to be expedient and possible for the azeotrope which is obtained when isopropanol is employed to be used directly as solvent, without removing water. However, preferably, the solvent is separated off at the same time as the water is removed, by spray-drying or spray-granulation.

A stable dry powder is obtained which is encased by a protective colloid which comprises at least one low-molecular-weight component and at least one high-molecular-weight component, whose mean molecular weights differ by at least 10,000. When a water-soluble colloid is used, this dry powder can be redissolved in water, achieving a uniform fine distribution of the active compound in the particle size range of less than 1 μm. In the photochemical stability test, the active compound hydrosol thus obtained, despite the fine distribution, proves to be extraordinarily stable.

Both in the aqueous xanthophyll dispersion and in the dry powder prepared therefrom, the active compound present has an amorphous content from 70 to 100%, determined from X-ray diffraction diagrams. In addition, the all-trans isomer content of the xanthophylls is at least 50%.

The preparations according to the invention are outstandingly suitable as food and feed colorants. Typical areas of use in the feed sector are, for example, pigmenting fish in aquaculture and pigmenting egg yolk and broiler skin in poultry rearing.

The examples illustrate the invention.

Example 1

In a heatable receiving flask, 40 g of astaxanthin and 15.4 g of peanut oil were suspended in a solution of 12.3 g of ethoxyquin in 288 g of isopropanol/water (88/12, w/w) at 30° C. This suspension was mixed in a mixing chamber at a mixing temperature of 170° C. with 587 g of isopropanol/water (88/12, w/w) with a residence time of 0.2 seconds. After said residence time, the resulting molecularly dispersed astaxanthin solution immediately afterward entered a further mixing chamber, in which, at a mixing angle of 90°, 11,340 g of an aqueous gelatin solution, adjusted to pH 9 which, in addition to 84 g of gelatin A (100 Bloom, $M_w$=94,000), contained 42 g of Gelita Sol P ($M_w$=21,000) and 92 g of sucrose, were added via a high-pressure pump, the astaxanthin precipitating out, at 45° C., in colloidally dispersed form having a mean particle size of 166 nm.

The dispersion was then concentrated and converted, in a manner known per se, into a free-flowing dry powder having a mean particle size of 237 nm. The dry powder redissolved in water, forming a clear red dispersion, the color strength of the redispersion having decreased only by approximately 10%, based on the original dispersion.

Comparative Example

In a heatable receiving flask, 40 g of astaxanthin and 15.4 g of peanut oil were suspended in a solution of 12.3 g of ethoxyquin in 288 g of isopropanol/water (88/12, w/w) at a temperature of 30° C. This suspension was mixed in a mixing chamber at a mixing temperature of 170° C. with 548 g of isopropanol/water (88/12, w/w) with a residence time of 0.2 seconds. After said residence time, the resulting molecularly dispersed astaxanthin solution entered a further mixing chamber, in which, at a mixing angle of 90°, 11,280 g of an aqueous gelatin solution, adjusted to pH 9, which, in addition to 126 g of gelatin-A (100 Bloom, $M_w$=94,000), contained 91 g of sucrose, were added via a high-pressure pump, the astaxanthin precipitating out, at a temperature of 45° C., in colloidally dispersed form having a mean particle size of 232 nm.

While the dispersion was being concentrated, active compound particles flocculated out, which was accompanied by a decrease in color strength to 60% of the initial value. By means of dynamic light scattering, mean particle sizes of 370 nm were measured. The dry powder prepared by a similar process in accordance with Example 1 was only partly redispersible.

We claim:

1. A process for preparing a stable aqueous dispersion, or a stable water-dispersible dry powder, of xanthophylls, which comprises
    a) preparing a molecularly dispersed solution of at least one xanthophyll, optionally an emulsifier and, optionally an edible oil and/or an edible oil, in a water-miscible organic solvent, or a mixture of water and a water-miscible organic solvent, at above 30° C.,
    b) mixing this solution with an aqueous solution of a mixture of protective colloids,
       $b_1$) in which the mixture comprises at least one low-molecular-weight protective colloid component and at least one high-molecular-weight protective colloid component whose mean molecular weights differ by at least 10,000,
       $b_2$) the solvent component being transferred to the aqueous phase and the hydrophobic phase of the xanthophyll being formed as an a nodisperse phase
    c) and, optionally, preparing a water-dispersible dry powder by freeing the resulting dispersion from the solvent and the water and drying it, optionally in the presence of a coating material.

2. A process as claimed in claim 1, wherein the proportion of the low-molecular-weight protein hydrolysate is from 5 to 95% by weight of the total amount of protective colloids.

3. A process as claimed in claim 1, wherein the molecularly dispersed solution of the xanthophyll is mixed in two steps with the aqueous protective-colloid-containing phase, the molecularly dispersed solution of the xanthophyll being mixed first only with the low-molecular-weight non-gelling protein hydrolysate and then with the high-molecular-weight gelling gelatine.

4. A stable aqueous xanthophyll dispersion produced by the process as claimed in claim 1.

5. A stable aqueous xanthophyll dispersion as claimed in claim 4, wherein said xanthophyll has an amorphous content of from 70 to 100%.

6. A stable aqueous xanthophyll dispersion as claimed in claim 4, wherein said xanthophyll has an all-trans isomer content of at least 50%.

7. A food, pharmaceutical or animal feed containing as an additive an aqueous stable dispersion of xanthophylls or a water dispersible dry powder of xanthophylls produced by the process as claimed in claim 1.

8. A stable water-dispersible xanthophyll dry powder which is encased by a protective colloid which comprises at least one low-molecular-weight non-gelling protein hydrolysate and at least one high-molecular-weight gelling gelatine whose mean molecular weights differ by at least 10,000.

\* \* \* \* \*

UNITED STATES PATENT AND TRADEMARK OFFICE
CERTIFICATE OF CORRECTION

PATENT NO. : 6,296,877 B1
DATED : October 2, 2001
INVENTOR(S) : Auweter et al.

It is certified that error appears in the above-identified patent and that said Letters Patent is hereby corrected as shown below:

Column 5,
Line 36, delete "and/or an edible oil";
Line 42, delete "protective colloid component" and insert -- non-gelling protein hydrolysate --.

Column 6,
Line 1, bridging line 2, delete "protective colloid component" and insert -- gelling gelatine --.
Line 6, delete "an a nodisperse" and insert -- nano-dispersant --.
Line 21, after "gelatine" insert -- and wherein the molecular weight of the non-gelling hydrolysate and the gelline gelatine differs at least 30,000 --.

Signed and Sealed this

Fifteenth Day of October, 2002

*Attest:*

JAMES E. ROGAN
*Attesting Officer*      *Director of the United States Patent and Trademark Office*